United States Patent [19]

Wada et al.

[11] Patent Number: 4,529,602
[45] Date of Patent: Jul. 16, 1985

[54] METHOD FOR TREATMENT OR PROPHYLAXIS OF GASTRO-INTESTINAL DISEASE

[75] Inventors: Hiroshi Wada, Omiya; Masatoshi Kawamori, Ageo; Hajime Tamaki, Sakado; Yuichi Onoda, Koshigaya, all of Japan

[73] Assignee: Tanabe Seiyaku Co., Ltd., Osaka, Japan

[21] Appl. No.: 621,124

[22] Filed: Jun. 14, 1984

Related U.S. Application Data

[63] Continuation of Ser. No. 432,968, Oct. 5, 1982, abandoned.

[30] Foreign Application Priority Data

Oct. 22, 1981 [GB] United Kingdom ............... 8131856
Jun. 29, 1982 [GB] United Kingdom ............... 8218707

[51] Int. Cl.$^3$ .............. A61K 31/19; A61K 27/00; A61K 31/495; A61K 31/40
[52] U.S. Cl. .................... 514/569; 544/107; 260/505 R; 514/555
[58] Field of Search ............ 260/505 R; 424/317, 424/248.5, 250, 274, 275, 273 R, 319; 544/107

[56] References Cited

U.S. PATENT DOCUMENTS 2,121,032  6/1938  Hasselstrom ............... 260/108
4,402,978  9/1983  Chrislidis et al. ............. 424/317

OTHER PUBLICATIONS

Freika Chem. Abst., vol. 75, 18, 9/25/51 7985a.
Enomoto et al., Chem. & Pharm. Bulletin, vol. 25, No. 3 (1977), pp. 507–510.

Primary Examiner—Alan Siegel
Attorney, Agent, or Firm—Jordan B. Bierman

[57] ABSTRACT

A method for the therapeutic treatment and/or prophylaxis of gastro-intestinal diseases using a sulfodehydroabietic acid of the formula:

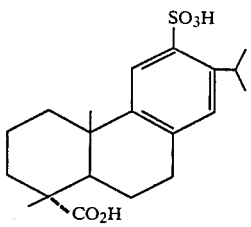

or a pharmaceutically acceptable salt thereof is disclosed.

10 Claims, No Drawings

METHOD FOR TREATMENT OR PROPHYLAXIS OF GASTRO-INTESTINAL DISEASE

This Application is a continuation of application Ser. No. 432,968 filed Oct. 5, 1982, abandoned, which claims the priority of British Application Nos. 8131856 and 8218707, filed Oct. 22, 1981 and June 29, 1982, respectively.

This invention relates to a novel method for the treatment or prophylaxis of gastro-intestinal diseases. More particularly, it relates to a method for the treatment or prophylaxis of gastro-intestinal diseases by administering to a warm-blooded animal sulfodehydroabietic acid of the formula:

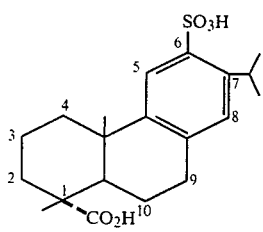

or a pharmaceutically acceptable salt thereof.

It is known that sulfodehydroabietic acid (I) (chemical name: 1,4a-dimethyl-1-carboxy-6-sulfo-7-isopropyl-1,2,3,4,4a,9,10,10a-octahydrophenanthrene) is prepared by sulfonation of pseudopimaric acid, pyroabietic acid or dehydroabietic acid (U.S. Pat. No. 2,121,032, J. Am. Chem. Soc., Vol. 60, pp. 2340–2341 (1938), ibid., Vol. 60, pp. 2631–2636 (1938) and ibid., Vol. 63, pp. 1838–1843 (1941)). It is also known that sodium and p-toluidine salts of sulfodehydroabietic acid are obtained by conventional neutralization of said abietic acid. Moreover, U.S. Pat. No. 2,121,032 discloses that sulfodehydroabietic acid (I) is useful as a detergent and wetting agent. However, no therapeutic effects of sulfodehydroabietic acid, or its salts, on gastro-intestinal diseases, have been known up to now.

We have now found that sulfodehydroabietic acid (I) and its salts show useful therapeutic effects on gastro-intestinal diseases. That is, they have a potent anti-peptic ulcer activity and are useful for the therapeutic treatment and/or prophylaxis of peptic ulcer diseases or gastritis. For example, sulfodehydroabietic acid (I) and its salts show preventive effects against pepsin secretion, gastric acid secretion, pylorus-ligated ulcers, drug-induced ulcers and stress-induced ulcers. Further, sulfodehydroabietic acid (I) and its salts increase mucosal resistance by enhancing gastric mucus secretion. Therefore, the compounds of the present invention can be used for the treatment and/or prophylaxis of a wide variety of gastro-intestinal diseases including gastritis and acute or chronic peptic ulcer diseases (e.g., gastric ulcer and duodenal ulcer). Moreover, the compounds of the present invention show no substantial mineralo-corticoid- or aldosterone-like effect and can be used without unfavorable side effects such as hypokalaemia. For example, when a test compound was administered orally to rats, sulfodehydroabietic acid monosodium salt, at a dose of 500 or 1000 mg/kg, showed no substantial change in urinary sodium-potassium ratio. Further, the toxicity of the compounds of the present invention are remarkably low. For example, the 50% lethal dose ($LD_{50}$) of sulfodehydroabietic acid monosodium salt, estimated by oral administration thereof to rats, was more than 2,000 mg/kg.

Salts of sulfodehydroabietic acid (I) which can be used for therapeutic treatment or prophylaxis of the above-mentioned gastro-intestinal diseases include the salts thereof with any pharmaceutically acceptable cation-forming substance. Such salts include, for example, those of sulfodehydroabietic acid (I) with metals, metal hydroxides or amines, and said amines may be either primary, secondary, tertiary or quaternary amines such as alkylamines, di-alkylamines, trialkylamines, alkylenediamines, cycloalkylamines, arylamines, aralkylamines, heterocyclic amines, α-amino acids, ω-amino acids, peptides or quaternary amines derived therefrom. In addition, these alkylamines, alkylenediamines, cycloalkylamines, aryl or aralkylamines, heterocyclic amines, amino acids and so forth may be optionally substituted with a group or groups selected from hydroxy, alkoxy, carboxy, acyl, acyloxy, aminoalkyl, alkylamino, alkyl, guanidino, carbamoyl, methylthio, mercapto, dialkyl-sulfonium and halogen groups; and further the amino acids or peptides may be, if required, in the form of the corresponding acid amides or esters. More specifically, for example, the salts of sulfodehydroabietic acid with metals or metal hydroxides includes the salts thereof with alkali metals such as sodium, lithium or potassium; alkali earth metals such as magnesium, calcium or barium; aluminum or aluminum hydroxides; and the like. The aluminum hydroxide salts may be sulfodehydroabietic acid (aluminum monohydroxide) or sulfodehydroabietic acid di(aluminum dihydroxide). Suitable examples of the salts of sulfodehydroabietic acid with mono-, di-, or trialkylamines include the salts thereof with alkylamines such as methylamine, ethylamine, propylamine or isopropylamine; dialkylamines such as dimethylamine, diethylamine or di-n-propylamine; trialkylamines such as trimethylamine or triethylamine; dialkylamino-alkylamines such as 2-dimethylaminoethylamine or 2-diethylaminoethylamine; alkoxy-alkylamines such as 2-methoxyethylamine or 3-ethoxy-n-propylamine; hydroxyalkylamines such as ethanolamine, 3-hydroxy-n-propylamine and the like. The salts of sulfodehydroabietic acid with the alkylenediamines include, for example, the salts thereof with ethylenediamine, trimethylenediamine, tetramethylenediamine, pentamethylenediamine, hexamethylenediamine and the like. The salts of sulfodehydroabietic acid with the cycloalkylamines include, for example, the salts thereof with cyclopropylamine, cyclobutylamine, cyclopentylamine, cyclohexylamine and the like. The salts of sulfodehydroabietic acid with the aralkylamines include, for example, the salts thereof with benzylamine, phenethylamine, 4-methoxyphenethylamine and the like. The salts of sulfodehydroabietic acid with the arylamines include, for example, the salts thereof with alkyl N-acyl-p-aminobenzoates such as ethyl N-piperidinoacetyl-p-aminobenzoate, ethyl N-prolyl-p-aminobenzoate, ethyl N-pipecolyl-p-aminobenzoate and the like. The salts of sulfodehydroabietic acid with the heterocyclic amines include, for example, the salts thereof with morpholine, piperazine, 3-(3,4-dihydroxyphenyl)-8,8-dimethyl-1,8-diazoniaspiro[4.5]decane, which is

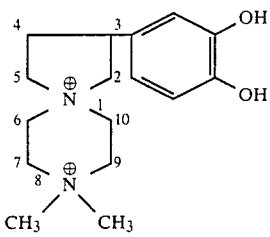

1-(2-dimethylaminoethyl)-4-phenyl-2-pyrrolidone, homocysteine thiolactone, 1-ethyl-2-aminomethyl-pyrrolidine and the like. Moreover, representative examples of the α- or ω-amino acids which can be used to form the salts with sulfodehydroabietic acid are shown by the formulae:

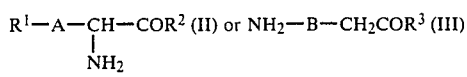

wherein $R^1$ is hydrogen, amino, guanidino, carbamoyl, dimethylsulfonio, 4-imidazolyl, mercapto or methylthio, $R^2$ is hydroxy, alkoxy, amino, alkylamino, dialkylamino, cycloalkylamino or p-alkoxyanilino, $R^3$ is hydroxy or alkoxy, A is single bond or straight or branched alkylene, and B is straight alkylene (said alkylene being optionally substituted with aryl). For example, said α- or ω-amino acids to be used in the present invention include lysine, ornithine, arginine, asparagine, glutamine, methionine, histidine, ethyl cysteinate, ethyl asparaginate, ethyl glutaminate, asparagine amide, glutamine amide, asparagine methylamide, glutamine methylamide, asparagine isopropylamide, glutamine isopropylamide, asparagine octylamide, glutamine octylamide, glutamine di-n-propylamide, asparagine cyclohexylamide, glutamine cyclohexylamide, asparagine p-methoxyanilide, glutamine p-methoxyanilide, S-methylmethionine (i.e., 3-(S,S-dimethylthionia)-α-aminobutyric acid), 6-aminocaproic acid, methyl 4-amino-3-phenylbutylate, and the like. Furthermore, suitable examples of the peptides which can be used to form the salts of the invention include dipeptides such as carnosine, homocarnosine (i.e., N-γ-aminobutyryl-histidine), anserin (i.e., N-β-alanyl-1-methylhistidine), balenin (i.e., N-β-alanyl-2-methylhistidine) and the like.

Of the above-mentioned various salts, a preferred subgenus is a salt of sulfodehydroabietic acid with an alkali metal; an alkali earth metal; aluminum; an aluminum hydroxide; or an amine selected from the group consisting of alkyl($C_{1-5}$)amine, di-alkyl($C_{1-5}$)amine, tri-alkyl($C_{1-5}$)amine, cycloalkyl($C_{3-6}$)amine, di-alkyl($C_{1-5}$)amino-alkyl($C_{1-5}$)amine, alkoxy($C_{1-5}$)-alkyl($C_{1-5}$)amine, hydroxy-alkyl($C_{1-5}$)amine, alkylene($C_{2-6}$)diamine, aralkyl($C_{7-8}$)amine, alkyl($C_{1-5}$)N-piperidinoacetyl-p-aminobenzoate, alkyl($C_{1-5}$)N-prolyl-p-aminobenzoate, alkyl($C_{1-5}$)N-pipecolyl-p-aminobenzoate, morpholine, piperazine, 3-(3,4-dihydroxyphenyl)-8,8-dimethyl-1,8-diazoniaspiro[4.5]decane, 1-(2-dimethylaminoethyl)-4-phenyl-2-pyrrolidone, homocysteine thiolactone, an α-amino acid of the formula (II) in which $R^1$ is amino, guanidino, carbamoyl, dimethyl sulfonio, 4-imidazolyl, mercapto or methylthio, $R^2$ is hydroxy, alkoxy($C_{1-5}$), amino, alkyl($C_{1-8}$)amino, di-alkyl($C_{1-5}$)amino, cycloalkyl($C_{3-6}$)amino or p-alkoxy($C_{1-5}$)anilino and A is straight alkylene($C_{1-5}$), a ω-amino acid of the formula (III) in which $R^3$ is hydroxy or alkoxy($C_{1-5}$) and B is straight alkylene($C_{1-5}$) (said alkylene being optionally substituted with phenyl), and carnosine.

Another preferred subgenus is a salt of sulfodehydroabietic acid with a metal selected from the group consisting of lithium, potassium, sodium, magnesium, calcium and aluminum; an aluminum hydroxide; or an amine selected from the group consisting of alkyl($C_{1-5}$)amine, cycloalkyl($C_{3-6}$)amine, di-alkyl($C_{1-5}$)amino-alkyl($C_{1-5}$)amine, alkoxy($C_{1-5}$)-alkyl($C_{1-5}$)amine, alkylene($C_{2-6}$)diamine, morpholine, arginine, glutamine, asparagine, lysine, S-methylmethionine and carnosine.

Further preferred subgenus is a salt of sulfodehydroabietic acid with sodium, calcium, aluminum, aluminum aluminum hydroxide, (2-dimethylaminoethyl)amine, cyclohexylamine, isopropylamine, morpholine, (2-methoxyethyl)amine, ethylenediamine, tetramethylenediamine, hexamethylenediamine, arginine, glutamine, asparagine, lysine, S-methylmethionine or carnosine.

Of the above-mentioned various salts, all sulfodehydroabietic acid salts except the sodium and p-toluidine salts thereof are novel compounds.

Pharmaceutically acceptable salts of sulfodehydroabietic acid (I) can be readily obtained. For example, the metal salt of sulfodehydroabietic acid (I) may be prepared by neutralizing the compound (I) with a metal hydroxide (e.g., sodium hydroxide, potassium hydroxide, lithium hydroxide, calcium hydroxide, aluminum hydroxide), a metal carbonate (e.g., sodium carbonate, potassium carbonate, lithium carbonate) or a metal bicarbonate (e.g., sodium bicarbonate, potassium bicarbonate) in a solvent. Water, methanol, ethanol, tetrahydrofuran, dimethylsulfoxide, dimethylformamide or a mixture thereof are suitable as the solvent. It is preferred to carry out the neutralization reaction at a temperature of 0° to 100° C. Further, sulfodehydroabietic acid monosodium salt can be prepared by treating sulfodehydroabietic acid disodium salt with an acid (e.g., hydrochloric acid). For example, sulfodehydroabietic acid disodium salt is dissolved in water, and the solution is then adjusted to a pH of 2.0 to 5.0, especially 3.7 to 3.8, with hydrochloric acid. The resultant precipitates are collected by a conventional method, for example, by filtration, whereby sulfodehydroabietic acid monosodium salt is obtained. Alternatively, sulfodehydroabietic acid monosodium salt can be prepared by partially neutralizing the compound (I) with sodium hydroxide, sodium bicarbonate, sodium carbonate or sodium acetate. Said partial neutralization reaction is preferably carried out by suspending sulfodehydroabietic acid in water, and then adjusting said suspension to a pH of 2.0 to 5.0, especially 3.7 to 3.8, by addition of sodium hydroxide, sodium bicarbonate, sodium carbonate or sodium acetate. The metal salt of sulfodehydroabietic acid (I) other than the sodium salt may be prepared by reacting sulfodehydroabietic acid sodium salt with a metal halide (e.g., calcium chloride, aluminum chloride), a metal sulfate (e.g., magnesium sulfate) or a metal nitrate (e.g., barium nitrate) in an aqueous solvent (e.g., water). Said reaction may be preferably carried out at a temperature of 0° to 100° C. Alternatively, the metal salt such as calcium and magnesium salts may be prepared by reacting sulfodehydroabietic acid silver salt with a metal halide (e.g., calcium chloride, magnesium chloride) in an aqueous solvent (e.g., water). It is preferred to carry out the reaction at a temperature of 0° to 100° C.

On the other hand, the aluminum hydroxide salt of sulfodehydroabietic acid (I) may be prepared by reacting the compound (I) with aluminum alkoxide (e.g., aluminum methoxide, aluminum ethoxide, aluminum isopropoxide) in the presence of water in a solvent. Methanol, ethanol, isopropanol and dimethylsulfoxide are suitable as the solvent. This reaction may be preferably carried out at a temperature of 0° to 60° C.

Further, the salts of sulfodehydroabietic acid (I) with the amine may also be prepared in the same manner as described above, i.e., by neutralizing the compound (I) with the amine in a solvent, or by reacting sulfodehydroabietic acid silver salt with a hydrohalide (e.g., hydrochloride) or quaternary salt of the amine in a solvent. Water, methanol, ethanol and the like are suitable as the solvent for the neutralization reaction. It is preferred to carry out the neutralization reaction at a temperature of 0° to 100° C. On the other hand, water is suitable as the solvent for the reaction of sulfodehydroabietic acid silver salt with the hydrohalide or quaternary salt of the amine, and said reaction may be preferably carried out at a temperature of 0° to 100° C.

Sulfodehydroabietic acid and its salts thereof are preferably administered in a solid dosage form such as tablets, capsules, powders or granules, or in a liquid dosage form such as solutions or suspensions. Sulfodehydroabietic acid and its salts may be administered either orally or parenterally, while it is generally preferred to administer them orally. In order to prepare pharmaceutical preparations suitable for oral administration, the active ingredient is worked up with pharmaceutical adjuvants or excipients. Suitable adjuvants for the solid dosage form such as tablets or capsules include, for example, binders (e.g., acacia, gelatin, dextrin, hydroxypropyl cellulose, methyl cellulose, polyvinylpyrrolidone), diluents (e.g., lactose, sucrose, mannitol, corn starch, potato starch, calcium phosphate, calcium citrate, crystalline cellulose), lubricants (e.g., magnesium stearate, calcium stearate, stearic acid, talc, anhydrous silicic acid), disintegrants (e.g., corn starch, potato starch, carboxymethyl cellulose and its calcium salt, alginic acid), wetting agents (e.g., sodium lauryl sulfate) and so forth. On the other hand, suitable adjuvants for the liquid dosage form such as solutions or suspensions include, for example, liquid vehicles (e.g., water), suspending agents (e.g., acacia, gelatin, methyl cellulose, sodium carboxymethyl cellulose, hydroxymethyl cellulose, aluminum stearate gel), surfactants (e.g., lecithin, sorbitan monooleate, glycerin monostearate), nonaqueous vehicles (e.g., glycerin, propylene glycol, vegetable oil) and so forth. The liquid dosage form may further contain preservatives (e.g., methyl p-hydroxybenzoate, propyl p-hydroxy benzoate), flavoring agents and/or coloring agents.

The therapeutic dose of sulfodehydroabietic acid (I) or its salt will of course vary with the conditions of diseases of patients to be treated and its severity. In general, however, it may be used at a dose of about 20 to about 300 mg, more especially about 40 to about 120 mg, per kilogram of body weight per day.

As mentioned hereinbefore, sulfodehydroabietic acid (I) or its salt shows potent anti-ulcer activity without aldosterone-like side effect and is useful for the treatment or prophylaxis of gastro-intestinal diseases, such as peptic ulcer diseases and gastritis, in warm-blooded animals, including man. The term "peptic ulcer disease" has historically been used to describe the diseases characterized by ulceration of the upper gastro-intestinal tract and include the diseases characterized by ulceration of the body of the stomach, commonly called gastric ulcers, as well as the diseases characterized by ulceration of the duodenum, commonly called duodenal ulcers. Accordingly, the term "peptic ulcer disease" used throughout the specification and claims should be interpreted to include both of the above-mentioned gastric ulcers and duodenal ulcers.

The following Experiments and Examples are merely for illustrative purposes and are not to be construed as limitations of the present invention.

EXPERIMENT 1

Preventive effect on acid and pepsin secretions (Method)

Male SD-strain rats (6 to 7 weeks old) were starved for 48 hours, and then the pylori were ligated. Immediately after ligation, a solution or suspension of a test compound in distilled water was administered orally into the stomachs in an amount of 0.2 ml per 100 g of body weight (Dose: 100 mg/kg). Five hours after said administration of the test compound, the rats were sacrificed and the stomachs were removed. The gastric contents were centrifuged at 2,500 rpm for 10 minutes and the gastric juice was collected as the supernatant. The concentration of pepsin in the gastric juice was determined by Anson's method (c.f., J. Gen. Physiol., 22, pp. 77–89 (1938)) using hemoglobin as the substrate, and the preventive effect of the test compound on the pepsin secretion was estimated in terms of "decrease in pepsin concentration" according to the following formula:

$$\text{Decrease (\%) in pepsin concentration} = \left[1 - \frac{\text{Average value of pepsin concentration in gastric juice of medicated rats}}{\text{Average value of pepsin concentration in gastric juice of non-medicated rats}}\right] \times 100$$

On the other hand, the concentration of free acid in the gastric juice was determined by titrating said gastric juice to pH 7.0 with 0.1N NaOH, and the preventive effect of the test compound on the gastric acid secretion was estimated in terms of "the decrease in acidity of gastric juice" according to the following formula:

$$\text{Decrease (\%) in acidity of gastric juice} = \left[1 - \frac{\text{Acid concentration in gastric juice of medicated rats}}{\text{Acid concentration in gastric juice of non-medicated rats}}\right] \times 100$$

(Results)

The results are shown in the following Tables 1 & 2.

TABLE 1

| Nos. | Salts of sulfodehydroabietic acid used | Decrease (%) in pepsin concentration |
|---|---|---|
| 1. | Monosodium salt | 96 |
| 2. | Disodium salt | 92 |
| 3. | Calcium salt | 99 |
| 4. | ⅔ Aluminum salt | 95 |
| 5. | 2 Aluminum dihydroxide salt | 69 |
| 6. | Aluminum monohydroxide salt | 91 |
| 7. | 2 (2-Dimethylaminoethyl)amine salt | 92 |

TABLE 1-continued

| Nos. | Salts of sulfodehydroabietic acid used | Decrease (%) in pepsin concentration |
|---|---|---|
| 8. | 2 Cyclohexylamine salt | 71 |
| 9. | 2 Isopropylamine salt | 95 |
| 10. | 2 Morpholine salt | 92 |
| 11. | 2 (2-Methoxyethyl)amine salt | 98 |
| 12. | Tetramethylenediamine salt | 84 |
| 13. | Ethylenediamine salt | 94 |
| 14. | Hexamethylenediamine salt | 94 |
| 15. | L-Arginine salt | 77 |
| 16. | L-Glutamine salt | 90 |
| 17. | L-Asparagine salt | 90 |
| 18. | L-Lysine salt | 94 |
| 19. | Carnosine salt | 72 |
| 20. | L-S—Methylmethionine salt | 84 |

TABLE 2

| Nos. | Salts of sulfodehydroabietic acid used | Decrease (%) in acidity of gastric juice |
|---|---|---|
| 1. | Monosodium salt | 43 |
| 2. | Disodium salt | 54 |
| 3. | Calcium salt | 30 |
| 4. | 2 (2-Dimethylaminoethyl)amine salt | 31 |
| 5. | 2 Isopropylamine salt | 40 |
| 6. | Tetramethylenediamine salt | 36 |
| 7. | Hexamethylenediamine salt | 32 |
| 8. | L-Glutamine salt | 39 |
| 9. | L-Asparagine salt | 38 |

EXPERIMENT 2

Effect on Shay rat ulcers (Method)

Male SD-strain rats (6 to 7 weeks old) were starved for 48 hours and then the pylori were ligated. Immediately after ligation, a solution or suspension of a test compound in distilled water was administered orally into the stomachs in an amount of 0.2 ml per 100 g of body weight (Dose: 200 or 300 mg/kg). Seventeen hours after the administration of the test compound, the degree of ulceration in forestomach was examined according to the method of Takagi et al (Chem. Pharm. Bull., 11(10), pp. 1282–1290 (1963)) with a modified scoring system. Depending on the diameter of each lesions, the ulcers were classified into the following 4 grades.

| | Ulcer score |
|---|---|
| Ulcer with diameter less than 1 mm | 1 point |
| Ulcer with diameter of 1–3 mm | 3 points |
| Ulcer with diameter of 3–5 mm | 5 points |
| Ulcer with diameter over 5 mm or perforation | 10 points |

Ulcer index was calculated by the sum of the number of ulcers in each degree multiplied by respective ulcer score.

Further, based on the ulcer index determined above, the preventive effect of the test compound on Shay rat ulcer was calculated by the following formula:

$$\text{Preventive effect on Shay rat ulcers (\%)} = \left[1 - \frac{\text{The average value of ulcer indexes in medicated rats}}{\text{The average value of ulcer indexes in non-medicated rats}}\right] \times 100$$

(Results)

The results are shown in the following Table 3.

TABLE 3

| Test compounds | Dose (mg/kg) | Preventive effect on Shay rat ulcers (%) |
|---|---|---|
| (The compounds of the present invention) | | |
| Sulfodehydroabietic acid monosodium salt | 200 | 100 |
| Sulfodehydroabietic acid disodium salt | 200 | 93 |
| Sulfodehydroabietic acid calcium salt | 300 | 100 |
| (Positive control) | | |
| Carbenoxolone disodium salt | 300 | 40 |

EXPERIMENT 3

Effect on stress-induced ulcers (Method)

Male ddY-strain mice (4 weeks old) weighing about 20 g were starved for about 7 hours. A solution of a test compound in distilled water was administered orally to the mice in an amount of 0.1 ml per 10 g of body weight (Dose: 100 mg/kg). Immediately after administration of the test compound, the mice were placed in a stress cage and immersed to the level of the cervix in a water bath (24±0.5° C.) for 16 hours. Then, the stomach was removed and slightly inflated by injecting 1.2 ml of a 1% formalin solution to fix the inner layers of the gastric walls. The stomach was then incised along the greater carvature, and the number of ulcerations was examined.

(Results)

Sulfodehydroabietic acid disodium salt showed 22% decrease in the number of stress-induced ulcers.

EXPERIMENT 4

Effect on aspirin-induced ulcers (Method)

Male Donryu-strain rats (8 to 9 weeks old) were starved overnight, and a solution or suspension of a test compound in distilled water was administered orally into the stomachs in an amount of one ml per 100 g of body weight. Half an hour later, a suspension of aspirin in 0.25% CMC solution was administered orally to the rats in an amount of 0.5 ml per 100 g of body weight (Dose: 200 mg/kg). Four hours after the administration of aspirin, the rats were sacrificed and the stomachs were removed and inflated by injecting 10 ml of 1% formalin solution to fix the inner layers of the gastric walls. The stomach was then incised along the greater curvature and the lengths of the lesions were measured and summated to give ulcer index (in mm) for each animal. The preventive effect of the test compound on aspirin-induced ulcers were calculated by the following formula:

$$\text{Preventive effect on aspirin induced ulcers (\%)} = \left[1 - \frac{\text{The average value of ulcer indexes in medicated rats}}{\text{The average value of ulcer indexes in non-medicated rats}}\right] \times 100$$

(Results)

The results are shown in the following Table 4.

TABLE 4

| Test compounds | Dose (p.o.) | Preventive effect on aspirin-induced ulcers (%) |
|---|---|---|
| Sulfodehydroabietic acid monosodium salt | 0.8 m mol./kg (400 mg/kg) | 68 |
| Sulfodehydroabietic acid carnosine salt | 2 m mol./kg (1,248 mg/kg) | 33 |
| Sulfodehydroabietic acid S—methylmethionine salt | 2 m mol./kg (1,086 mg/kg) | 85 |
| Sulfodehydroabietic acid disodium salt | 2 m mol./kg (847 mg/kg) | 82 |

EXPERIMENT 5

(Effect on gastric mucus secretion)

Stimulating effect of a test compound on gastric mucus secretion was examined by the method of Corne et al. (J. Physiol., 242, pp. 116–117(1974); J. Pharm. Pharmacol., 33, pp. 348–352(1981)). Male Sprague-Dawley rats (6–7 weeks old; one group: 6 rats) were fasted for 20 hours before the experiments. Water was given ad libitum and coprophagy was prevented by using cages with wide-mesh floors. A test compound dissolved or suspended in distilled water was administered orally to the rats at a dose of 100 mg/kg. One hour after the administration of the test compound, the stomachs were dissected, opened along the greater curvature, rinsed in ice-cold 0.25M sucrose, and the rumen was discarded. Then, the stomachs were incubated in 10 ml of a 0.15M sucrose-0.05M sodium acetate solution (pH 5.8) containing alcian blue (1 mg/ml), at room temperature for 1.5 hours. Finally, the stomachs were placed in 15 ml of a 0.5M magnesium chloride solution for 2 hours with occasional shaking and then removed, and the magnesium chloride solution was shaken briefly with 10 ml of diethyl ether. The optical density of the aqueous layer was read at 605 nm, and the degree of alcian blue binding was expressed as μg alcian blue/g of tissue. The stimulating effect of the test compound on gastric mucus secretion was estimated in terms of "the increase in alcian blue binding" which was calculated by the following formula:

$$\text{Increase (\%) in alcian blue binding} = \left[ \frac{\mu g \text{ alcian blue/g tissue in medicated rats}}{\mu g \text{ alcian blue/g tissue in non-medicated rats}} - 1 \right] \times 100$$

(Results)

The results are shown in the following Table 5.

TABLE 5

| Test compounds | Stimulating effect on gastric mucus secretion | |
|---|---|---|
| | Alcian blue binding (μg/g tissue) | Increase (%) in alcian blue binding |
| Control (water) | 198.5 ± 6.4 | — |
| Sulfodehydroabietic acid monosodium salt | 287.3 ± 34.2 | 45 |
| Sulfodehydro abietic acid disodium salt | 247.7 ± 18.4 | 25 |
| Sulfodehydroabietic acid calcium salt | 284.7 ± 14.9 | 44 |

EXPERIMENT 6

(protective effect on gastric mucous membrane)

Protective effect of a test compound on gastric mucous membrane was examined by the method of Diago et al. (Yakugaku Zasshi, 101, 452–457(1981)). Male Sprague-Dawley rats (6–7 weeks old; one group: 5 rats) were fasted for 20 hours before the experiments. Water was given ad libitum and coprophagy was prevented by using cages with wide-mesh floors. The stomach was excised, opened along the greater curvature, rinsed in physiological saline solution, and the rumen was discarded. The stomach was incubated in 10 ml of an artificial gastric juice (100 mM HCl, 0.3% pepsin, 0.2% NaCl) containing a test compound, at 37° C. for 60 minutes. After the incubation, 2 ml of 7% trichloroacetic acid were added to 0.5 ml of medium, and the mixture was centrifuged. The amount of tyrosine in the supernatant was measured by using Folin-Ciocelteu reagent (J. gen. Physiol., 16, 59–63(1932)), and expressed as mg tyrosine/g tissue. The protective effect of the test compound on gastric mucous membrane was estimated in terms of "the inhibition of digestion of mucous membrane" which was calculated by the following formula:

$$\text{Inhibition (\%) of digestion of mucous membrane} = \left[ 1 - \frac{\text{mg tyrosine/g tissue estimated by adding test compound}}{\text{mg tyrosine/g tissue estimated without adding test compound}} \right] \times 100$$

(Results)

The results are shown in the following Table 6.

TABLE 6

| Test compound | Concentration in artificial gastric juice (mg/ml) | Protective effect on gastric mucous membrane | |
|---|---|---|---|
| | | Amount of tyrosine (mg/g tissue) | Inhibition (%) of digestion of mucous membrane |
| Control (no addition) | — | 2.42 ± 0.15 | — |
| Sulfodehydroabietic acid monosodium salt | 1 | 1.61 ± 0.13 | 33 |
| | 4 | 0.95 ± 0.07 | 61 |
| Sulfodehydroabietic acid disodium salt | 1 | 1.64 ± 0.12 | 32 |
| | 4 | 0.82 ± 0.07 | 66 |
| Sulfodehydroabietic acid calcium salt | 1 | 1.72 ± 0.08 | 29 |
| | 4 | 0.86 ± 0.04 | 64 |

EXPERIMENT 7

Effect on urine volume and urinary electrolytes (Method)

Male SD-strain rats (6 to 7 weeks old) were starved overnight, and a physiological saline solution (3 ml/100 g of body weight) was orally administered to the rats. One hour later, a solution or suspension of a test compound in a 0.25% CMC-physiological saline solution was administered orally to the rats in an amount of 3 ml per 100 g of body weight (Dose: 50 and 500 mg/kg). Immediately after administration of the test compound, the rats were placed into metabolic cages (2 rats per cage) and deprived of water and food for 5 hours. The urine samples which were excreted during a 5 hour period were collected. Sodium and potassium in the urine were estimated by a flame photometer (Hitachi Model-205).

(Results)

The results are shown in the following Table 7.

TABLE 7

| Test compounds | Dose (mg/kg) | Urine volume (ml) | Na/K |
| --- | --- | --- | --- |
| (The test compound of the present invention) | | | |
| Sulfodehydroabietic acid calcium salt | 50 | 11.5 | 5.2 |
| | 500 | 11.3 | 6.8 |
| Carbenoxolone disodium salt | 50 | 9.3 | 3.2 |
| Control | — | 12.3 | 5.8 |

Carbenoxolone (chemical name: 3-$\beta$-hydroxy-11-oxoolean-12-en-30-oic acid hydrogen succinate)-disodium salt is known to protect animals from experimentally-induced gastric ulceration and, in human gastric ulcer patients, has been shown, in numerous clinical trials, to be an effective gastric anti-ulcer agent. However, carbenoxolone disodium salt has an aldosterone-like side effect. As can be seen from Table 7, the compound of the present invention is quite free from such side effect.

EXPERIMENT 8

Effect on urinary electrolytes (Method)

Male SD-strain rats (6 to 7 weeks old, one group: 5-8 rats) were starved overnight, and a physiological saline solution (3 ml/100 g of body weight) was orally administered to the rats. One hour later, a solution of a test compound in a 0.25% CMC-physiological saline solution was administered orally to the rats in an amount of 3 ml per 100 g of body weight (Dose: 50, 500 or 1,000 mg/kg). Immediately after administration of the test compound, the rats were placed into metabolic cages (one rat per cage) and deprived of water and food for 4 hours. The urine samples which were excreted during a 4 hour period were collected. Sodium and potassium in the urine were estimated by a flame photometer (Hitachi Model-205).

(Results)

The results are shown in the following Table 8.

TABLE 8

| Test compound | Dose mg/kg p.o. | Urine volume (ml) | Na/K ratio |
| --- | --- | --- | --- |
| Sulfodehydroabietic acid disodium salt | 500 | 4.8 ± 0.4 | 7.4 ± 1.0 |
| | 1000 | 4.3 ± 0.3 | 5.9 ± 0.4 |
| Carbenoxolone disodium salt | 50 | 5.2 ± 0.3 | 3.7 ± 0.3* |
| Control | — | 5.7 ± 0.6 | 6.1 ± 0.3 |

* = significantly different ($p < 0.01$) from control

EXPERIMENT 9

Effect on urinary electrolytes (Method)

Male SD-strain rats (6 to 7 weeks old, one group: 6 rats) were starved overnight, and a physiological saline solution (3 ml/100 g of body weight) was orally administered to the rats. One hour later, a suspension of a test compound in a physiological saline solution was administered orally to the rats in an amount of 3 ml per 100 g of body weight (Dose: 500 or 1,000 mg/kg). Immediately after administration of the test compound, the rats were placed into metabolic cages (one rat per cage) and deprived of water and food for 4 hours. The urine samples which were excreted during a 4 hour period were collected. Sodium and potassium in the urine were estimated by a flame photometer (Hitachi Model-205).

(Results)

The results are shown in the following Table 9.

TABLE 9

| Test Compound | Dose mg/kg | Urine volume (ml) | Na/K ratio |
| --- | --- | --- | --- |
| Sulfodehydroabietic acid monosodium salt | 500 | 6.2 ± 0.5 | 5.6 ± 0.5 |
| | 1000 | 4.7 ± 0.4 | 5.9 ± 0.2 |
| Control (physiological saline) | — | 6.5 ± 0.3 | 5.8 ± 0.6 |

EXPERIMENT 10

After male SD-strain rats (6–7 weeks old) were starved for 20 hours, a solution or suspension of a test compound in distilled water was administered orally to the rats in an amount of one ml per 100 g of body weight. After administration of the test compound, the rats were allowed free access to water and food. The mortality of the rats was observed for 7 days and the 50% lethal dose ($LD_{50}$) was calculated therefrom.

The results are shown in the following Table 10.

TABLE 10

| Test compounds | $LD_{50}$ (mg/kg) |
| --- | --- |
| Sulfodehydroabietic acid monosodium salt | >2000 |
| Sulfodehydroabietic acid disodium salt | >2000 |
| Sulfodehydroabietic acid calcium salt | >2000 |

EXPERIMENT 11

After male ddY-strain mice (4 weeks old) were starved for 4 hours, a suspension of a test compound in distilled water containing a small amount of Tween 80 was administered orally to the mice in an amount of 0.1 ml per 10 g of body weight. After administration of the test compound, the mice were allowed free access to water and food. The mortality of the mice was observed for 7 days and the 50% lethal dose ($LD_{50}$) was calculated therefrom. As a result, the $LD_{50}$ of sulfodehydroabietic acid calcium salt was more than 2,000 mg/kg.

EXAMPLE 1

10 g of sulfodehydroabietic acid hemihydrate (chemical name: 1,4a-dimethyl-1-carboxy-6-sulfo-7-isopropyl-1,2,3,4,4a,9,10,10a-octahydro-phenanthrene hemihydrate) is suspended in 50 ml of water, and 2.1 g of sodium hydroxide are added thereto under stirring. The mixture is treated with activated charcoal, and then condensed to a total volume of 20 ml under reduced pressure. The condensed solution is heated to make a clear solution which is allowed to stand at room temperature. The crystalline precipitates are collected by filtration and then dried in air. 10.4 g of sulfodehydrobietic acid disodium salt 8½ hydrate (chemical name: 1,4a-dimethyl-1-carboxy-6-sulfo-7-isopropyl-1,2,3,4,4a,9,10,-10a-octahydro-phenanthrene disodium salt 8½ hydrate) is thereby obtained.

m.p. >300° C.
$[\alpha]_D^{20} = +48.2°$ (C=2.5, H$_2$O)
IR$\nu_{max}^{nujol}$ (cm$^{-1}$): 3483 (broad), 1540, 1461, 1377, 1192, 1158, 1097, 1067

Concomitantly, the crystalline precipitates mentioned above are dried over phosphorus pentoxide at 160° C. under a pressure of 3 mm Hg for 17 hours, whereby sulfodehydroabietic acid disodium salt anhydrate is obtained.

M.p. >300° C.
$[\alpha]_D^{20} = +64.6°$ (C=2.5, H$_2$O)
IR$\nu_{max}^{KBr}$ (cm$^{-1}$): 1556, 1485, 1395, 1185, 1098, 1059, 1046

Sulfodehydroabietic acid disodium salt 8½ hydrate, obtained above, is recrystallized from an aqueous 95% methanol solution and then dried in air, whereby sulfodehydroabietic acid disodium salt ½ hydrate is obtained.

M.p. >300° C.
$[\alpha]_D^{20} = +58.2°$ (C=2.5, H$_2$O)
IR$\nu_{max}^{nujol}$ (cm$^{-1}$): 3444 (broad), 1583, 1570, 1461, 1407, 1380, 1229, 1195, 1174, 1098, 1061, 1045, 1034

EXAMPLE 2

5 g of sulfodehydroabietic acid disodium salt anhydrate (chemical name: 1,4a-dimethyl-1-carboxy-6-sulfo-7-isopropyl-1,2,3,4,4a,9,10,10a-octahydro-phenanthrene disodium salt anhydrate) is dissolved in 50 ml of water and the solution is adjusted to pH 3,7 with about 12 ml of 1N-hydrochloric acid. The precipitates are collected by filtration, dried in air and then recrystallized from water. 3.87 g of sulfodehydroabietic acid monosodium salt 5 hydrate (chemical name: 1,4a-dimethyl-1-carboxy-6-sulfo-7-isopropyl-1,2,3,4,4a,9,10,-10a-octahydro-phenanthrene monosodium salt 5 hydrate) is thereby obtained.

M.p. >300° C.
$[\alpha]_D^{20} = +59.4°$ (C=0.5, H$_2$O)
IR$\nu_{max}^{Nujol}$ (cm$^{-1}$): 3513–3421 (broad), 1689, 1633 1461, 1377, 1276, 1197, 1187, 1163, 1097, 1058, 1048, 1037

When the precipitates are recrystallized from ethanol, instead of water, sulfodehydroabietic acid monosodium salt 6/7 hydrate containing 3/4 ethanol is obtained.

M.p. >300° C.
$[\alpha]_D^{20} = +66.2°$ (C=0.5, H$_2$O)
IR$\nu_{max}^{Nujol}$ (cm$^{-1}$): 3418 (broad), 1712, 1461, 1385, 1247, 1211, 1190, 1166, 1137, 1100, 1034, 1008

EXAMPLE 3

6.1 g of sulfodehydroabietic acid is suspended in 15 ml of water, and the suspension is adjusted to pH 3.72 by adding about 13.5 ml of an aqueous 1N sodium hydroxide solution thereto under stirring. The mixture is heated to make a clear solution which is allowed to stand at room temperature. The crystalline precipitates are collected by filtration and then dried in air. 5.5 g of sulfodehydroabietic acid monosodium salt 5 hydrate is thereby obtained.

The physico-chemical properties of the product are identical with those of the product obtained in Example 2.

EXAMPLE 4

3.98 of sulfodehydroabietic acid is suspended in 20 ml of water, and 0.5 g of sodium bicarbonate is added thereto. Then, 1.35 g of sodium chloride are added to the mixture and said mixture is heated. Water is added to the mixture until said mixture becomes a clear solution. The solution is allowed to stand at room temperature. The crystalline precipitates are collected by filtration and then recrystallized from water. 3.5 g of sulfodehydroabietic acid monosodium salt 5 hydrate is thereby obtained.

The physico-chemical properties of the product are identical with those of the product obtained in Example 2.

EXAMPLE 5

1.36 g of sulfodehydroabietic acid monohydrate is dissolved in 10 ml of ethanol, and a solution of 288 mg of lithium hydroxide monohydrate in 3 ml of water is added thereto under cooling. 100 ml of acetone are added to the mixture and the precipitates are collected therefrom. 1.4 g of sulfodehydroabietic acid dilithium salt monohydrate is obtained.

M.p. >300° C.
IR$\nu_{max.}^{nujol}$ (cm$^{-1}$): 3430, 1540, 1400, 1160

EXAMPLE 6

1.36 g of sulfodehydroabietic acid monohydrate and 0.383 g of potassium hydroxide are treated in the same manner as described in Example 5, whereby 1.3 g of sulfodehydroabietic acid dipotassium salt monohydrate is obtained.

M.p. >300° C.
IR$\nu_{max.}^{nujol}$ (cm$^{-1}$): 3500–3200 (broad), 1530, 1190

EXAMPLE 7

To the solution of 5 g of sulfodehydroabietic acid disodium salt anhydrate in 20 ml of water is added a solution of 1.5 g of calcium chloride in 10 ml of water. The precipitated solid is filtered, washed with a small amount of water and air dried. The dried solid is immersed in 20 ml methanol and the undissolved materials are removed. The methanol solution is warmed to boiling and 4 ml of water are added thereto. After cooling, the precipitated crystals are filtered, washed with water and air dried to give 2.5 g of sulfodehydroabietic acid calcium salt 2.5 hydrate.

M.p. >300°
$[\alpha]_D^{20} = +54.8°$ (C=0.5, MeOH)
IR$\nu_{max}^{nujol}$ (cm$^{-1}$): 3535, 3354 (br.), 1544, 1464 1401, 1379, 1229, 1216, 1190, 1100, 1061, 1046

EXAMPLE 8

5 g of sulfodehydroabietic acid is dissolved in 200 ml of water and 1.25 g of calcium chloride in 25 ml of water are added dropwise thereto. When the clear solution is warmed to 80°–85° C., crystals are precipitated slowly. After the precipitation is completed, the crystals are filtered while hot, washed with hot water and air dried to give 3.5 g of sulfodehydroabietic acid calcium salt 2.5 hydrate.

The physico-chemical properties of the product are identical with those of the product obtained in Example 7.

EXAMPLE 9

5 g of sulfodehydroabietic acid disodium salt anhydrate is dissolved in 20 ml of water and 1.56 g of magnesium sulfate in 10 ml of water are added thereto. The solvent is distilled to half of its original volume and the precipitated solids are filtered, washed with water and air dried. The dried solids are recrystallized from water to give 3.99 g of sulfodehydroabietic acid magnesium salt 7.4 hydrate.

M.p. > 300°
$[\alpha]_D^{20} = +50.9°$ (C=2.5, H$_2$O)
IR$\nu_{max}^{nujol}$(cm$^{-1}$): 3413 (br.), 1678, 1517, 1461, 1390, 1169, 1097, 1056, 1045, 1034

EXAMPLE 10

1.32 g of sulfodehydroabietic acid disodium salt anhydrate is dissolved in 6 ml of water and a 50% aqueous aluminum chloride solution is added dropwise thereto until precipitation completes. 2 ml of ethanol are added to the mixture and the precipitates are collected, washed with water and ethanol and then dried. 1.0 g of sulfodehydroabietic acid 2/3 aluminum ssalt 7/3 hydrate is obtained.

M.p. > 300° C.
IR$\nu_{max}^{nujol}$(cm$^{-1}$): 3500–3100 (br.), 1600, 1440, 1200, 1150, 1030

EXAMPLE 11

A solution of 1.62 g of aluminum isopropoxide in 12 ml of ethanol and 0.288 g of water are added to 10 ml of an ethanol solution containing 1.52 g of sulfodehydroabietic acid monohydrate and the mixture is concentrated under reduced pressure to dryness. 1.71 g of sulfodehydroabietic acid di(aluminum dihydroxide)salt dihydrate is obtained as colorless crystalline powder.

M.p. > 300° C.
IR$\nu_{max}^{nujol}$(cm$^{-1}$): 3400 (br), 1570, 1440, 1200, 1160, 1100, 1050, 1030

EXAMPLE 12

1.36 g of sulfodehydroabietic acid monohydrate is dissolved in 10 ml of methanol and 404 mg of isopropylamine are added thereto. The mixture is evaporated under reduced pressure to remove the solvent. The residue is recrystallized from methanol, whereby 1.4 g of sulfodehydroabietic acid di(isopropylamine)salt is obtained as needles.

M.p. > 300° C.
IR$\nu_{max}^{nujol}$ (cm$^{-1}$): 2750–2500, 1610, 1520, 1380, 1190, 1160, 1020

EXAMPLE 13

1.3 g of sulfodehydroabietic acid monohydrate and 0.2 g of cyclohexylamine are treated in the same manner as described in Example 12, whereby 0.9 g of sulfodehydroabietic acid di(cyclohexylamine)salt is obtained as needles.

M.p. > 300° C. (recrystallized from methanol)
IR$\nu_{max}^{nujol}$ (cm$^{-1}$): 2800–2400, 1625, 1510, 1370, 1210, 1135, 1020

EXAMPLE 14

1.3 g of sulfodehydroabietic acid monohydrate and 0.36 g of 2-dimethylaminoethylamine are treated in the same manner as described in Example 12, whereby 0.8 g of sulfodehydroabietic acid di(2-dimethylaminoethylamine)salt monohydrate is obtained as needles.

M.p. 240°–242° C. (decomp.) (recrystallized from ethanol-tetrahydrofuran)
IR$\nu_{max}^{nujol}$ (cm$^{-1}$): 3500–3050, 2780–2300, 1620, 1520, 1190, 1180, 1150, 1020

EXAMPLE 15

1.3 g of sulfodehydroabietic acid monohydrate and 0.2 g of morpholine are treated in the same manner as described in Example 12, whereby 1.24 g of sulfodehydroabietic acid dimorpholine salt hemihydrate is obtained as needles.

M.p. 288°–290° C. (decomp.) (recrystallized from methanol-acetone)
IR$\nu_{max}^{nujol}$ (cm$^{-1}$): 3600–3300, 2750–2500, 1630, 1360, 1180, 1140, 1100, 1030

EXAMPLE 16

1.3 g of sulfodehydroabietic acid monohydrate and 0.353 g of piperazine are treated in the same manner as described in Example 12, whereby 0.82 g of sulfodehydroabietic acid piperazine salt hemihydrate is obtained as needles.

M.p. > 300° C.
IR$\nu_{max}^{nujol}$ (cm$^{-1}$): 3450, 2750–2500, 1630, 1180, 1095, 1035

EXAMPLE 17

1.3 g of sulfodehydroabietic acid monohydrate and 0.616 g of 2-methoxyethylamine are treated in the same manner as described in Example 12, whereby 0.98 g of sulfodehydroabietic acid di(2-methoxyethylamine)salt is obtained as needles.

M.p. 275°–277° C. (recrystallized from methanol-ethyl acetate)
IR$\nu_{max}^{nujol}$ (cm$^{-1}$): 3400–3050, 2750–2150, 1630, 1520, 1160, 1115, 1030

EXAMPLE 18

1.3 g of sulfodehydroabietic acid monohydrate and 0.994 g of phenethylamine are treated in the same manner as described in Example 12, whereby 1.42 g of sulfodehydroabietic acid di(phenethylamine)salt is obtained as needles.

M.p. 281°–284° C. (decomp.) (recrystallized from methanol)
IR$\nu_{max}^{nujol}$ (cm$^{-1}$): 3400–3000, 2800–2100, 1630, 1480, 1360, 1190, 1170, 1030

EXAMPLE 19

1.3 g of sulfodehydroabietic acid monohydrate and 0.21 g of ethylenediamine are treated in the same manner as described in Example 12, whereby 0.6 g of sulfodehydroabietic acid ethylenediamine salt hemihydrate is obtained as small needles.

M.p. 279°–280° C. (decomp.) (recrystallized from ethanol-tetrahydrofuran)

IR$\nu_{max}^{nujol}$ (cm$^{-1}$): 3450, 2750–2300, 1650, 1585, 1180, 1150, 1025

EXAMPLE 20

1.3 g of sulfodehydroabietic acid monohydrate and 0.298 g of tetramethylenediamine are treated in the same manner as described in Example 12, whereby 1.06 g of sulfodehydroabietic acid tetramethylenediamine salt hemihydrate is obtained.

M.p. 284°–287° C. (decomp.) (recrystallized from methanol-aqueous tetrahydrofuran)

IR$\nu_{max}^{nujol}$ (cm$^{-1}$): 3550–3400, 2800–2100, 1610, 1500, 1360, 1160, 1025

EXAMPLE 21

1.3 g of sulfodehydroabietic acid monohydrate and 0.4 g of hexamethylenediamine are treated in the same manner as described in Example 12, whereby 0.77 g of sulfodehydroabietic acid hexamethylenediamine salt hemihydrate is obtained.

M.p. 290° C. (decomp.) (recrystallized from water-acetone)

IR$\nu_{max}^{nujol}$ (cm$^{-1}$): 3530, 3490, 2750–2300, 1615, 1510, 1375, 1190, 1160, 1020

EXAMPLE 22

2.6 g of sulfodehydroabietic acid monohydrate is dissolved in 20 ml of methanol and a solution of 0.94 g of L-lysine in 10 ml of water is added thereto. The mixture is concentrated under reduced pressure to dryness. The residue is recrystallized from a mixture of methanol and water, whereby 3 g of sulfodehydroabietic acid L-lysine salt monohydrate is obtained as a crystalline solid.

M.p. 236° C. (decomp.)

IR$\nu_{max}^{nujol}$ (cm$^{-1}$): 3400, 1680, 1590, 1165

EXAMPLE 23

1.3 g of sulfodehydroabietic acid monohydrate and 0.45 g of L-ornithine are treated in the same manner as described in Example 22, whereby 1.4 g of sulfodehydroabietic acid L-ornithine salt monohydrate is obtained as a crystalline solid.

M.p. 213°–215° C. (recrystallized from methanol)

IR$\nu_{max}^{nujol}$ (cm$^{-1}$): 3400, 3160–3100, 2750–2200, 1700, 1650, 1190, 1150

EXAMPLE 24

2.85 g of sulfodehydroabietic acid monohydrate and 1.75 of L-arginine acetate are treated in the same manner as described in Example 22, whereby 2.9 g of sulfodehydroabietic acid L-arginine salt hemihydrate is obtained as colorless prisms.

M.p. 230° C. (decomp.) (recrystallized from methanol-water)

IR$\nu_{max}^{nujol}$ (cm$^{-1}$): 3350, 3200, 3100, 1680–1630 (br), 1180

EXAMPLE 25

1.3 g of sulfodehydroabietic acid monohydrate and 0.513 g of L-asparagine are treated in the same manner as described in Example 22, whereby 1.5 g of sulfodehydroabietic acid L-asparagine salt monohydrate is obtained as a crystalline solid.

M.p.>300° C. (recrystallized from water)

IR$\nu_{max}^{nujol}$ (cm$^{-1}$): 3400–3200, 2750–2300, 1740, 1680, 1270, 1170

EXAMPLE 26

1.3 g of sulfodehydroabietic acid monohydrate and 0.5 g of L-glutamine are treated in the same manner as described in Example 22, whereby 1.1 g of sulfodehydroabietic acid L-glutamine salt hemihydrate is obtained as a crystalline solid.

M.p.>240° C. (crystallized from methanol-acetone)

IR$\nu_{max}^{nujol}$ (cm$^{-1}$): 3400–3100, 2750–2300, 1750, 1690, 1670, 1590, 1240, 1200, 1170, 1140

EXAMPLE 27

1.3 g of sulfodehydroabietic acid monohydrate and 0.51 g of L-methionine are treated in the same manner as described in Example 22, whereby 1.4 g of sulfodehydroabietic acid L-methionine salt is obtained as a crystalline solid.

M.p. 250°–252° C. (decomp.) (recrystallized from methanol-ethyl acetate)

IR$\nu_{max}^{nujol}$ (cm$^{-1}$): 3450–3050, 2800–2300, 1750, 1690, 1280, 1200, 1190, 1160

EXAMPLE 28

1.3 g of sulfodehydroabietic acid monohydrate and 0.64 g of L-histidine are treated in the same manner as described in Example 22, whereby 1.0 g of sulfodehydroabietic acid L-histidine salt monohydrate is obtained as a crystalline solid.

M.p. 225° C.(decomp.) (recrystallized from methanol-water)

IR$\nu_{max}^{nujol}$ (cm$^{-1}$): 3400–3100, 2750–2300, 1690, 1610, 1160

EXAMPLE 29

1.3 g of sulfodehydroabietic acid is dissolved in 15 ml of ethanol and 0.472 mg of silver carbonate and 20 ml of water are added thereto. 0.635 g of ethyl L-cysteinate hydrochloride are added to the mixture and said mixture is stirred at room temperature. The precipitates are filtered off and the filtrate is concentrated to dryness under reduced pressure. The residue is recrystallized from a mixture of methanol and ethyl acetate, whereby 1.5 g of sulfodehydroabietic acid ethyl L-cysteinate salt hemihydrate is obtained.

M.p. 239°–241° C. (decomp.)

IR$\nu_{max}^{nujol}$ (cm$^{-1}$): 3400–3100, 2750–2400, 1750, 1690, 1210, 1150, 1030

EXAMPLE 30

1.3 g of sulfodehydroabietic acid, 0.472 g of silver carbonate and 0.672 g of ethyl L-asparaginate hydrochloride are treated in the same manner as described in Example 29, whereby 0.9 g of salt of sulfodehydroabietic acid ethyl L-asparaginate salt is obtained.

M.p.>260° C. (decomp.) (recrystallized from ethanol-ethyl acetate)

IR$\nu_{max}^{nujol}$ (cm$^{-1}$): 3450, 3300, 3200, 2800–2400, 1760, 1710, 1690, 1610, 1250, 1190, 1160

EXAMPLE 31

1.31 g of sulfodehydroabietic acid, 0.472 g of silver carbonate and 0.93 g of ethyl L-glutaminate hydrochloride are treated in the same manner as described in Example 29, whereby 0.8 g of sulfodehydroabietic acid ethyl L-glutaminate salt monohydrate is obtained.

M.P. 254° C. (decomp.) (recrystallized from water-ethanol)

IR$\nu_{max.}^{nujol}$ (cm$^{-1}$): 3500–3050, 2750–2300, 1740, 1690–1640, 1200, 1180, 1160, 1140

EXAMPLE 32

1.3 g of sulfodehydroabietic acid, 0.472 g of silver carbonate and 0.526 g of L-homocysteine thiolactone hydrochloride are treated in the same manner as described in Example 29, whereby 1.4 g of sulfodehydroabietic acid L-homocysteine thiolactone salt is obtained.

M.p. 289°–291° C. (decomp.) (recrystallized from methanol-ethyl acetate)

IR$\nu_{max.}^{nujol}$ (cm$^{-1}$): 3400, 3150, 2750–2400, 1710, 1505, 1185, 1150, 1030

EXAMPLE 33

1.3 g of sulfodehydroabietic acid, 0.5 g of silver carbonate and 0.573 g of L-asparagine amide hydrochloride are treated in the same manner as described in Example 29, whereby 0.9 of sulfodehydroabietic acid L-asparagine amide salt is obtained.

M.p. >300° C. (recrystallized from ethanol)

IR$\nu_{max.}^{nujol}$ (cm$^{-1}$): 3400–3200, 2750–2300, 1690, 1650, 1605, 1195, 1155

EXAMPLE 34

1.3 g of sulfodehydroabietic acid, 0.5 g of silver carbonate and 0.621 g of L-glutamine amide hydrochloride are treated in the same manner as described in Example 29, whereby 1.14 g of sulfodehydroabietic acid L-glutamine amide salt hemihydrate is obtained.

M.p. >300° C. (recrystallized from methanol-ethyl acetate)

IR$\nu_{max.}^{nujol}$ (cm$^{-1}$): 3370, 3200, 2800–2300, 1690, 1650, 1530, 1200, 1165, 1100

EXAMPLE 35

1.52 g of sulfodehydroabietic acid monohydrate is dissolved in 5 ml of methanol, and a solution of 0.907 g of L-glutamine cyclohexylamide in 20 ml of methanol is added thereto. The mixture is concentrated under reduced pressure to remove solvent until the volume of said mixture is 5 ml. Ether is added to the residue and the precipitates (white crystalline) are collected therefrom. 1.35 g of sulfodehydroabietic acid L-glutamine cyclohexylamide salt hemihydrate is thereby obtained.

M.p. >190° C. (decomp.)

IR$\nu_{max.}^{nujol}$ (cm$^{-1}$): 3400, 3210, 3070, 2750–2300, 1695, 1670, 1650, 1570, 1255, 1180, 1160

EXAMPLE 36

1.14 g of sulfodehydroabietic acid monohydrate and 0.435 g of L-asparagine methylamide are treated in the same manner as described in Example 35, whereby 1.3 g of sulfodehydroabietic acid L-asparagine methylamide salt is obtained.

M.p. 240° C. (decomp.) (recrystalllized from ethanol-ether)

IR$\nu_{max.}^{nujol}$ (cm$^{-1}$): 3430–3050, 2750–2300, 1710, 1680, 1630, 1560, 1180, 1170, 1140

EXAMPLE 37

1.14 g of sulfodehydroabietic acid monohydrate and 0.73 g of L-asparagine n-octylamide are treated in the same manner as described in Example 35, whereby 1.2 g of sulfodehydroabietic acid L-asparagine n-octylamide salt hemihydrate is obtained as crystalline powder.

M.p. >87° C. (decomp.)

IR$\nu_{max.}^{nujol}$ (cm$^{-1}$): 3400–3100, 2750–2300, 1700, 1680, 1655, 1620, 1560, 1180, 1160, 1140

EXAMPLE 38

1.14 g of sulfodehydroabietic acid monohydrate and 0.525 g of L-asparagine isopropylamide are treated in the same manner as described in Example 35, whereby 1.42 g of sulfodehydroabietic acid L-asparagine isopropylamide salt is obtained.

M.p. 141° C. (decomp.) (recrystallized from ethano-lacetone)

EXAMPLE 39

1.14 g of sulfodehydroabietic acid monohydrate and 0.639 g of L-asparagine cyclohexylamide are treated in the same manner as described in Example 35, whereby 1.4 g of sulfodehydroabietic acid L-asparagine cyclohexylamide salt monohydrate is obtained.

M.p. 228° C. (decomp.) (recrystallized from ethano-lacetone)

IR$\nu_{max.}^{nujol}$ (cm$^{-1}$): 3430–3100, 2800–2300, 1690, 1680, 1660, 1620, 1560, 1215, 1160, 1140

EXAMPLE 40

1.12 g sulfodehydroabietic acid monohydrate and 0.7 g of L-asparagine p-methoxyanilide are treated in the same manner as described in Example 35, whereby 1.4 g of sulfodehydroabietic acid L-asparagine p-methoxyanilide salt hemihydrate is obtained as powder.

M.p. >170° C. (decomp.)

IR$\nu_{max.}^{nujol}$ (cm$^{-1}$): 3450–3050, 2750–2300, 1690, 1655, 1620, 1610, 1550, 1510, 1240, 1170,

EXAMPLE 41

1.14 g of sulfodehydroabietic acid monohydrate and 0.771 g of L-glutamine n-octylamide are treated in the same manner as described in Example 35, whereby 1.42 g of sulfodehydroabietic acid L-glutamine n-octylamide salt monohydrate is obtained.

M.p. 141° C. (decomp.)

IR$\nu_{max.}^{nujol}$ (cm$^{-1}$): 3450–3100, 2750–2250, 1690, 1660, 1570, 1510, 1200, 1180, 1130

EXAMPLE 42

1.14 g of sulfodehydroabietic acid monohydrate and 0.567 g of L-glutamine isopropylamide are treated in the same manner as described in Example 35, whereby 1.62 g of sulfodehydroabietic acid L-glutamine isopropylamide salt hemihydrate is obtained.

M.p. >190° C. (decomp.) (recrystallized from ethano-lacetone)

IR$\nu_{max.}^{nujol}$ (cm$^{-1}$): 3500–3050, 2750–2300, 1700, 1670, 1610, 1550, 1520, 1255, 1210, 1160, 1140, 1100

EXAMPLE 43

1.04 g of sulfodehydroabietic acid monohydrate and 0.63 g of L-glutamine di-n-propylamide are treated in the same manner as described in Example 35, whereby 0.6 g of sulfodehydroabietic acid L-glutamine di-n-propylamide salt monohydrate is obtained.

M.p. >139° C. (decomp.) (recrystallized from methanol-ether)

IR$\nu_{max.}^{nujol}$ (cm$^{-1}$): 3400–3100, 2750–2300, 1700, 1660, 1240, 1200, 1160

EXAMPLE 44

11.6 g of S-methyl-L-methionine iodide is dissolved in 50 ml of water and the solution and passed through a column packed with 100 ml of a weakly basic ion exchange resin (manufactured by Rohm & Hass Co. under the trade name "Amberlite IR 45"). Then, the column is washed with about 200 ml of water. The effluent and washings are combined and a solution of 15.2 g of sulfodehydroabietic acid monohydrate in 150 ml of methanol is added to the combined solution. The mixture is concentrated to dryness at a temperature below 50° C. under reduced pressure. The residue is dissolved in 200 ml of a 50% aqueous ethanol solution and 800 ml of acetone are added thereto. The mixture is allowed to stand at room temperature. The precipitates are collected, whereby 18 g of sulfodehydroabietic acid S-methyl-L-methionine salt dihydrate is obtained as crystals.

M.p. 268° C. (decomp.)

IR$\nu_{max.}^{nujol}$ (cm$^{-1}$): 3460, 3340, 1695, 1680, 1630, 1520, 1230, 1210, 1170, 1140, 1035

EXAMPLE 45

1.53 g of sulfodehydroabietic acid monohydrate is suspended in 17.6 ml of water and a solution of 0.85 g of carnosine in 3.3 ml of water is added thereto under stirring. The mixture is heated to make a solution and the hot solution is filtered with charcoal. The filtrate is allowed to stand at room temperature, whereby 2.2 g of sulfodehydroabietic acic carnosine salt monohydrate is obtained as needles.

M.p. 190°–224° C. (decomp.)

IR$\nu_{max.}^{nujol}$ (cm$^{-1}$): 3600–3100, 2800–2300, 1700, 1660, 1630, 1230, 1200, 1170

EXAMPLE 46

1.3 g of sulfodehydroabietic acid monohydrate and 0.448 g of 6-aminocaproic acid are treated in the same manner as described in Example 22, whereby 1.1 g of sulfodehydroabietic acid 6-aminocaproic acid salt is obtained.

M.p. 220°–222° C. (decomp.) (recrystallized from methanol-water)

IR$\nu_{max.}^{nujol}$ (cm$^{-1}$): 3300, 3070, 2750–2300, 1710, 1670, 1210, 1160

EXAMPLE 47

1.14 g of sulfodehydroabietic acid monohydrate and 0.87 g of ethyl N-piperidinoacetyl-p-aminobenzoate are treated in the same manner as described in Example 12, whereby 1.4 g of the salt (monohydrate) of sulfodehydroabietic acid with ethyl N-piperidinoacetyl-p-aminobenzoate is obtained.

M.p. 171° C. (recrystallized from ethanol-water)

IR$\nu_{max.}^{nujol}$ (cm$^{-1}$): 3500–3080, 2750–2300, 1700, 1680, 1605, 1550, 1280, 1210, 1150, 1115

EXAMPLE 48

1.3 g of sulfodehydroabietic acid monohydrate and 0.862 g of ethyl N-L-prolyl-p-aminobenzoate are treated in the same manner as described in Example 12, whereby 1.1 g of the salt of sulfodehydroabietic acid with ethyl N-L-prolyl-p-aminobenzoate is obtained.

M.p. 273°–275° C. (recrystallized from methanol)

IR$\nu_{max.}^{nujol}$ (cm$^{-1}$): 3430, 3300–3100, 1715–1705, 1605, 1550, 1280, 1210, 1180, 1150

EXAMPLE 49

1.2 g of sulfodehydroabietic acid monohydrate and 0.83 g of ethyl N-pipecolyl-p-aminobenzoate are treated in the same manner as described in Example 12, whereby 0.8 g of the salt (monohydrate) of sulfodehydroabietic acid with ethyl N-pipecolyl-p-aminobenzoate is obtained.

M.p. 230° C. (decomp.) (recrystallized from ethanol-ether)

IR$\nu_{max.}^{nujol}$ (cm$^{-1}$): 3430–3050, 2750–2300, 1700, 1675, 1600, 1545, 1270, 1200, 1180, 1150, 1100

EXAMPLE 50

1.14 g of sulfodehydroabietic acid monohydrate, 0.4 g of silver carbonate and 0.66 g of 3-(3,4-dihydroxyphenyl)-8,8-dimethyl-1,8-diazoniaspiro[4.5]decane dibromide are treated in the same manner as described in Example 29, whereby 0.8 g of the salt of sulfodehydroabietic acid with ½ 3-(3,4-dihydroxyphenyl)-8,8-dimethyl-1,8-diazoniaspiro[4.5]decane is obtained as crystalline powder.

M.P. 265° C. (decomp.) (recrystallized from methonolethylacetate)

IR$\nu_{max.}^{nujol}$ (cm$^{-1}$): 3500–3200, 1700, 1600, 1520, 1250, 1200, 1150, 1130, 1030,

EXAMPLE 51

1.14 g of sulfodehydroabietic acid monohydrate and 0.7 g of 1-(2-dimethylaminoethyl)-4-phenyl-2-pyrrolidone are treated in the same manner as described in Example 12, whereby 1.30 g of the salt of sulfodehydroabietic acid with 1-(2-dimethylaminoethyl)-4-phenyl-2-pyrrolidone is obtained.

M.P. 216°–218° C. (decomp.) (recrystallized from ethanol-ether)

IR$\nu_{max.}^{nujol}$ (cm$^{-1}$): 3400, 2750–2400, 1720, 1690, 1600, 1260, 1200, 1130, 1030

EXAMPLE 52

1.14 g of sulfodehydroabietic acid monohydrate and 0.58 g of methyl 4-amino-3-phenylbutylate are treated in the same manner as described in Example 12, whereby 0.7 g of the salt of sulfodehydroabietic acid with methyl 4-amino-3-phenylbutylate is obtained.

M.P. 242° C. (decomp.) (recrystallized from a mixture of methanol and ether)

IR$\nu_{max.}^{nujol}$ (cm$^{-1}$): 3300–3050, 1720, 1700, 1630, 1520, 1240, 1180, 1160, 1030

EXAMPLE 53

(Tablets)

| | |
|---|---|
| Sulfodehydroabietic acid monosodium salt | 250 g |
| Corn starch | 25 g |

The mixture of these ingredients is granulated with the aid of 10 g of hydroxypropyl cellulose (a binding agent). Twelve g of crystalline cellulose and 3 g of magnesium stearate are added to the resultant granules and the mixture is then compressed into tablets of suitable concaved form (10 mm in diameter, weight 300 mg).

EXAMPLE 54

(Granules)

| Sulfodehydroabietic acid monosodium salt | 100 g |
|---|---|
| Corn starch | 5 g |

The mixture of these ingredients is granulated with the aid of 5 g of polyvinylpyrrolidone (a binding agent) and the resultant granules is passed through a standard sieve (840μ aperture) to give granules containing 1000 mg of said monosodium salt per 1100 mg of granules.

EXAMPLE 55

(Capsules)

| Sulfodehydroabietic acid monosodium salt | 500 g |
|---|---|
| Corn starch | 50 g |
| Crystalline cellulose | 47 g |
| Magnesium stearate | 3 g |

The above-mentioned ingredients are thoroughly mixed and the mixture is encapsulated to give capsules containing 600 mg of said mixture per each capsules.

What we claim is:

1. A method for the treatment or prophylaxis of a peptic ulcer disease or gastritis disease in a warm-blooded animal which comprises administering to said animal a therapeutically effective amount of sulfodehydroabietic acid of the formula:

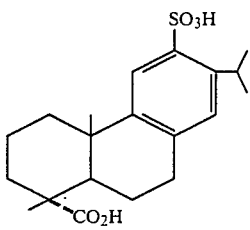

or a pharmaceutically acceptable salt thereof.

2. The method according to claim 1, wherein a pharmaceutically acceptable salt of sulfodehydroabietic acid is administered.

3. The method according to claim 2, wherein said pharmaceutically acceptable salt is a salt of sulfodehydroabietic acid with sodium, calcium, aluminum, aluminum hydroxide, (2-dimethylaminoethyl)amine, cyclohexylamine, isopropylamine, morpholine, (2-methoxyethyl)amine, ethylenediamine, tetramethylenediamine, hexamethylenediamine, arginine, glutamine, asparagine, lysine, S-methylmethionine or carnosine.

4. The method according to claim 2, wherein said pharmaceutically acceptable salt is sulfodehydroabietic acid monosodium salt.

5. The method according to claim 2, wherein said pharmacetically acceptable salt is sulfodehydroabietic acid disodium salt.

6. The method according to claim 2, wherein said pharmaceutically acceptable salt is sulfodehydroabietic acid calcium salt.

7. The method according to claim 2, 3, 4, 5 or 6, wherein the pharmaceutically acceptable salt of sulfodehydroabietic acid is administered at a dose of 20 to 300 mg per kilogram of body weight per day.

8. The method according to claim 2, 3, 4, 5, 6 or 7, wherein the pharmaceutically acceptable salt of sulfodehydroabietic acid is administered at a dose of 40 to 120 mg per kilogram of body weight per day.

9. The method according to claim 2, wherein said pharmaceutically acceptable salt is a salt of sulfodehydroabietic acid with an alkali metal; an alkaline earth metal; aluminum; an aluminum hydroxide; or an amine selected from the group consisting of
   1. alkylamine, di-alkylamine, tri-alkylamine, di-alkylamino-alkylamine, alkoxy-alkylamine, hydroxy-alkylamine, alkyl N-piperidinoacetyl-p-aminobenzoate, alkyl N-propyl-p-aminobenzoate, alkyl N-pipecolyl-p-aminobenzoate,
   2. cycloalkylamine,
   3. alkylenediamine,
   4. aralkylamine,
   5. morpholine, piperazine,

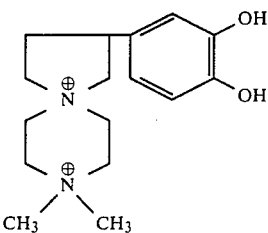

1-(2-dimethyl-aminoethyl)-4-phenyl-2-pyrrolidone, homocysteine thiolactone,
   6. an α-amino acid of the formula:

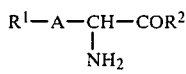

wherein $R^1$ is amino, guanidino, carbamoyl, dimethylsulfonio, 4-imidazolyl, mercapto or methylthio, $R^2$ is hydroxy,
   a. alkoxyamino, di-alkylamino, p-alkoxyanilino,
   b. alkylamino,
   c. cycloalkylamino,
   and A is straight chain alkylene of 1 to 5 carbon atoms,
   7. an ω-amino acid of the formula:

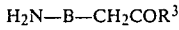

wherein $R^3$ is hydroxy or alkoxy of 1 to 5 carbon atoms and B is straight alkylene of 1 to 5 carbon atoms, said alkylene of B being optionally substituted with phenyl, and
   8. carnosine, wherein said alkyl and alkoxy moieties of groups (1) and (a) have 1 to 5 carbon atoms, said cycloalkyl moiety of groups (2) and (c) have 3–6 carbon atoms, said alkylene moiety of group (3) has 2–6 carbon atoms, said aralkyl moiety has 7–8 carbon atoms and said alkyl moiety of group (b) has 1–8 carbon atoms.

10. The method of claim 9 wherein said pharmaceutically acceptable salt is selected from the group consisting of lithium, potassium, sodium, magnesium, calcium and aluminum, an aluminum hydroxide and an amine selected from the group consisting of
   9. alkylamine, di-alkylamino-alkylamine, alkoxy-alkylamine,
   10. cycloalkylamine,
   11. alkylenediamine,
   12. morpholine,
   13. arginine,
   14. glutamine 15. asparagine
16. lysine
17. S-methyl-methionine and
18. carnosine, wherein said alkyl and alkoxy moiety of group (9) have 1–5 carbon atoms, said cycloalkyl moiety of group (10) has 3–6 carbon atoms, and said alkylene moiety of group (11) has 2–6 carbon atoms.

* * * * *